United States Patent
Baek et al.

(10) Patent No.: US 12,409,164 B2
(45) Date of Patent: Sep. 9, 2025

(54) ORALLY DISINTEGRATED TABLET COMPRISING CARBAMATE COMPOUND

(71) Applicant: SK BIOPHARMACEUTICALS CO., LTD., Gyeonggi-do (KR)

(72) Inventors: Myoung Ki Baek, Gyeonggi-do (KR); So Young Choi, Gyeonggi-do (KR); Ji Hye Lee, Gyeonggi-do (KR)

(73) Assignee: SK BIOPHARMACEUTICALS CO., LTD., Gyeonggi-Do (KR)

( * ) Notice: Subject to any disclaimer, the term of this patent is extended or adjusted under 35 U.S.C. 154(b) by 459 days.

(21) Appl. No.: 16/469,268

(22) PCT Filed: Dec. 14, 2017

(86) PCT No.: PCT/KR2017/014731
§ 371 (c)(1),
(2) Date: Jun. 13, 2019

(87) PCT Pub. No.: WO2018/111002
PCT Pub. Date: Jun. 21, 2018

(65) Prior Publication Data
US 2021/0085646 A1  Mar. 25, 2021

(30) Foreign Application Priority Data
Dec. 14, 2016  (KR) .................. 10-2016-0170434

(51) Int. Cl.
*A61K 31/41*  (2006.01)
*A61K 9/00*   (2006.01)
*A61K 9/20*   (2006.01)

(52) U.S. Cl.
CPC ............ *A61K 31/41* (2013.01); *A61K 9/0056* (2013.01); *A61K 9/2018* (2013.01); *A61K 9/2027* (2013.01); *A61K 9/2054* (2013.01); *A61K 9/2059* (2013.01)

(58) Field of Classification Search
CPC .... A61K 9/2054; A61K 9/2027; A61K 31/16; A61K 9/2059; A61K 9/0056; A61K 31/41; A61K 9/2018; A61P 25/06; A61P 25/24; A61P 25/08
See application file for complete search history.

(56) References Cited

U.S. PATENT DOCUMENTS

| | | | |
|---|---|---|---|
| 2005/0169986 A1* | 8/2005 | Tian | A61K 9/2077 424/464 |
| 2006/0258718 A1* | 11/2006 | Choi | A61P 25/30 514/359 |
| 2010/0233278 A1* | 9/2010 | Ookawa | A61K 9/0056 424/494 |
| 2012/0282335 A1* | 11/2012 | Venkatesh | A61K 31/5513 424/465 |
| 2015/0252398 A1 | 9/2015 | Lim et al. | |

FOREIGN PATENT DOCUMENTS

| EP | 2308464 A1 | 4/2011 |
|---|---|---|
| JP | 2006 070046 A | 3/2006 |
| KR | 10-2008-0005437 A | 1/2008 |
| KR | 10-2010-0031282 A | 3/2010 |
| KR | 10-1046789 B1 | 7/2011 |
| KR | 10-2014-0001236 A | 1/2014 |
| WO | WO-2014-106962 A1 | 7/2014 |

OTHER PUBLICATIONS

Bialer, et al. (2015) Progress report on new antiepileptic drugs: A summary of the Twelfth Eilat Conference (EILAT XII). *Epilepsy Research*, 111:85-141.
Supplementary European Search Report, issued May 20, 2020 for corrresponding European Patent Application No. 17879982.1.
International Search Report from corresponding PCT Application No. PCT/KR2017/014731, mailed on Mar. 21, 2018, with English translation.

* cited by examiner

*Primary Examiner* — Doan T Phan
(74) *Attorney, Agent, or Firm* — Harness, Dickey & Pierce, P.L.C.

(57) ABSTRACT

The present invention relates to an orally disintegrated tablet and a method for producing same, the tablet containing a carbamate compound of chemical formula 1, an isomer thereof, or a pharmaceutically acceptable salt, a solvate or a hydrate thereof, as an active ingredient.

19 Claims, 5 Drawing Sheets

|  | Comparative Example 2 | Example 2 |
|---|---|---|
| Initial |  |  |
| 1 hr |  |  |
| 3 hrs |  |  |

Comparative Example 2
50x magnification of
the resulting disintegrated
solution

Example 2
50x magnification of
the resulting disintegrated
solution

Comparative Example 2
200x magnification of
the resulting disintegrated
solution Example 2
200x magnification of
the resulting disintegrated
solution

ORALLY DISINTEGRATED TABLET COMPRISING CARBAMATE COMPOUND

CROSS-REFERENCE TO RELATED APPLICATIONS

This application is a national phase application of PCT Application No. PCT/KR2017/014731, filed on Dec. 14, 2017, which claims the benefit and priority to Korean Patent Application No. 10-2016-0170434, filed on Dec. 14, 2016. The entire disclosures of the applications identified in this paragraph are incorporated herein by references.

FIELD

The present invention relates to an orally disintegrating tablet comprising a carbamate compound of the following Formula 1, an isomer thereof, or a pharmaceutically acceptable salt, solvate or hydrate thereof as an active ingredient, and a preparation method thereof:

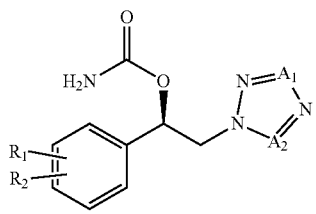

[Formula 1]

wherein,
$R_1$, $R_2$, $A_1$ and $A_2$ are as defined herein.

BACKGROUND

The carbamate compound of Formula 1 and the method for preparing the same are described in detail in PCT Publication Nos. WO 2006/112685 A1, WO 2010/150946 A1 and WO 2011/046380 $A_2$, the disclosures of which are incorporated herein by reference. One specific embodiment of the carbamate compound of Formula 1 includes carbamic acid (R)-1-(2-chlorophenyl)-2-(tetrazol-2-ypethyl ester of the following Formula 2:

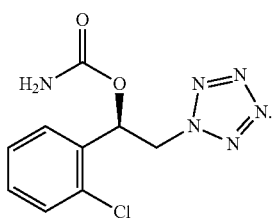

[Formula 2]

The carbamate compound of Formula 1 or 2 is known to be effective in the treatment of epilepsy.

Administration of a general immediate-release tablet containing the carbamate compound of Formula 1 or 2 may be difficult to take if it is prescribed to epileptic patients who are afraid to swallow.

People who are afraid to swallow because of dysphagia or fear of choking are not confined to young people and older people but have a wide age distribution, and about 35% of the world's population are afraid of swallowing. In addition, the development of a solid formulation that does not need to be swallowed due to its prompt integration in the oral cavity without water intake is of great interest to the general population as well as to patients who have difficulty swallowing, such as elderly persons, infants, mental patients and uncooperative patients.

Prescribing medicine for oral administration to people who are uncomfortable or have trouble in swallowing may cause a negative effect on the treatment because it may delay or prevent the consumption of medicine. In addition, in the case of drug for treating epilepsy, blood concentration of the drug should be maintained above the therapeutic concentration to prevent further seizures. If the drug is not administered on time, it cannot prevent the recurrence of further seizures. Such a situation is even more fatal because it can lead to an emergency involving severe nerve damage and after-effects.

Orally disintegrating tablets are disintegrated within a few seconds with only a small amount of saliva in the oral cavity, so it is not necessary to swallow tablets. Hence, medication compliance of patients who are afraid to swallow can be improved. Further, as foreign body sensation and residual feeling in the oral cavity are minimized, it is easier for the patient to adhere to his/her medication compliance. Therefore, there has been a continuous demand for developing a manufacturing technique of orally disintegrating tablet that minimizes foreign body sensation and residual feeling. However, if the hardness of the tablet is too low to rapidly disintegrate, the tablets will be easily worn out, which makes it difficult to transport and store. If the hardness is made high in order to compensate the above, the disintegration time in the oral cavity may be delayed. Hence, a manufacturing technique of an orally disintegrating tablet having appropriate hardness is necessary.

The following prior arts are known in the development of tablets that dissolve or disintegrate in the oral cavity.

Zydis, an orally disintegrating tablet developed and commercialized by RP Scherer, has the advantage of being rapidly disintegrated in the oral cavity. However, since it is prepared using freeze-drying technology, it is difficult to ensure the stability of the product during the distribution process due to physical impact.

Korean Patent Laid-Open Publication No. 2001-0006835 discloses a method for preparing orally disintegrating tablets by a direct compression method using spray-dried mannitol as a disintegrant and crospovidone as a co-disintegrant. However, this method is disadvantageous in that the dissolution rate in the oral cavity is relatively lower than those of the above techniques.

Korean Patent Laid-Open Publication No. 2010-0008419 discloses a method for preparing orally disintegrating tablets which improves stability by dry mixing of amlodipine after wet granulation of excipients to improve water instability of amlodipine. However, in the case of an active ingredient having no reduction in stability due to moisture, there is a disadvantage in that a content irregularity may occur due to a difference in particle size between the wet granule and the active ingredient.

Therefore, with regard to the carbamate compound of Formula 1 or 2, in order to improve medication compliance of epileptic patients who are afraid to swallow the tablets and try to delay or avoid ingestion of the tablets, it is necessary to develop an orally disintegrating tablet that exhibits preferable disintegration rate and hardness, shows uniform content of the active ingredient and minimizes foreign body sensation and residual feeling in the oral cavity.

DISCLOSURE

Problem to be Solved

The present invention is intended to provide an orally disintegrating tablet and preparation method thereof for improving medication compliance of patients who are afraid to swallow, wherein the orally disintegrating tablet comprises a carbamate compound of Formula 1 or 2 as an active ingredient, exhibits rapid disintegration in the oral cavity and excellent hardness, friability and storage stability, and minimizes foreign body sensation and residual feeling in the oral cavity.

Technical Solution to the Problem

The present inventors have found that if the granules are prepared by wet granulation by adding a hydrophilic excipient and a disintegrant to the carbamate compound of Formula 1 or 2 and then adding the disintegrant to the granules and mixing them, the prepared orally integrating tablet shows high hardness and low friability as well as fast disintegration rate, and also minimizes foreign body sensation and residual feeling.

Accordingly, the present invention provides an orally disintegrating tablet comprising:

(i) a granule prepared by wet granulation to comprise the following ingredients:
  (1) a carbamate compound of the following Formula 1, an isomer thereof, or a pharmaceutically acceptable salt, solvate or hydrate thereof as an active ingredient;
  (2) a hydrophilic excipient consisting of a first hydrophilic excipient of a sugar alcohol; and a second hydrophilic excipient selected from the group consisting of starch, microcrystalline cellulose, hydroxypropylcellulose and lactose; and
  (3) a disintegrant; and (ii) a disintegrant which is mixed with the granule of (i):

[Formula 1]

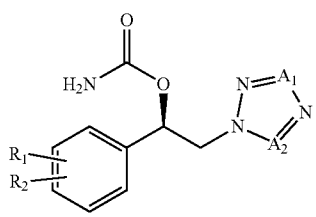

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In one embodiment of the present invention, in Formula 1, $R_1$ and $R_2$ are each independently selected from the group consisting of hydrogen, halogen and $C_1$-$C_8$ alkyl.

In one embodiment, the halo-$C_1$-$C_8$ alkyl is perfluoroalkyl.

In one embodiment of the present invention, the carbamate compound of Formula 1 is carbamic acid (R)-1-(2-chlorophenyl)-2-(tetrazol-2-yl)ethyl ester of the following Formula 2:

[Formula 2]

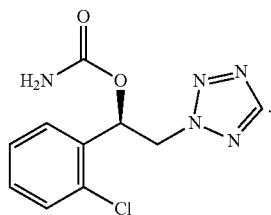

In one embodiment of the present invention, the first hydrophilic excipient of a sugar alcohol is selected from the group consisting of mannitol, sorbitol, xylitol, lactitol, maltitol and erythritol.

In one embodiment of the present invention, the disintegrant in the above (i) and (ii) is selected from the group consisting of sodium starch glycolate, croscarmellose sodium, low substituted hydroxypropylcellulose and crospovidone.

Accordingly, in one embodiment, the present invention provides an orally disintegrating tablet comprising:

(i) a granule prepared by wet granulation to comprise the following ingredients:
  (1) a carbamate compound of Formula 1, an isomer thereof, or a pharmaceutically acceptable salt, solvate or hydrate thereof as an active ingredient;
  (2) a hydrophilic excipient consisting of a first hydrophilic excipient of a sugar alcohol selected from the group consisting of mannitol, sorbitol, xylitol, lactitol, maltitol and erythritol; and a second hydrophilic excipient selected from the group consisting of starch, microcrystalline cellulose, hydroxypropylcellulose and lactose; and
  (3) a disintegrant selected from the group consisting of sodium starch glycolate, croscarmellose sodium, low substituted hydroxypropylcellulose and crospovidone; and (ii) a disintegrant selected from the group consisting of sodium starch glycolate, croscarmellose sodium, low substituted hydroxypropylcellulose and crospovidone, which is mixed with the granule of (i).

In one embodiment of the present invention, the content of the carbamate compound is 2.5 to 25 wt % based on the total weight of the orally disintegrating tablet.

In one embodiment of the present invention, the content of the hydrophilic excipient is 65 to 90 wt % based on the total weight of the orally disintegrating tablet.

In one embodiment of the present invention, the weight ratio of the first hydrophilic excipient and the second hydrophilic excipient is 2:1 to 10:1, and preferably 4:1 to 8:1.

In one embodiment of the present invention, the content of the disintegrant in the granule of (i) is 1 to 10 wt %, and preferably 2 to 5 wt % based on the total weight of the orally disintegrating tablet.

In one embodiment of the present invention, the disintegrant mixed in (ii) contains 60 to 80% of particles having a particle size of 40 to 600 μm, and the content thereof is 4 to 8 wt % based on the total weight of the orally disintegrating tablet.

In one embodiment of the present invention, the orally disintegrating tablet is used for the treatment of anxiety, depression, convulsion, epilepsy, migraine, bipolar disorder, drug abuse, smoking, attention deficit hyperactivity disorder (ADHD), obesity, sleep disorders, neuropathic pain, stroke, cognitive disorders, neurodegeneration or muscle spasm.

In addition, the present invention provides a method for preparation of an orally disintegrating tablet, comprising:

(a) a step of mixing the following ingredients (1) to (3);
(1) a carbamate compound of the following Formula 1, an isomer thereof, or a pharmaceutically acceptable salt, solvate or hydrate thereof as an active ingredient;
(2) a hydrophilic excipient consisting of a first hydrophilic excipient of a sugar alcohol; and a second hydrophilic excipient selected from the group consisting of starch, microcrystalline cellulose, hydroxypropylcellulose and lactose; and
(3) a disintegrant;
(b) a step of preparing a granule by wet granulation using the mixture of step (a);
(c) a step of mixing the granule obtained from step (b) with a disintegrant; and
(d) a step of lubricating and tableting the mixture obtained from step (c):

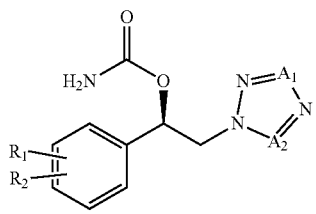

[Formula 1]

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In one embodiment of the present invention, in Formula 1, $R_1$ and $R_2$ are each independently selected from the group consisting of hydrogen, halogen and $C_1$-$C_8$ alkyl.

In one embodiment, the halo-$C_1$-$C_8$ alkyl is perfluoroalkyl.

In one embodiment of the present invention, the carbamate compound of Formula 1 is carbamic acid (R)-1-(2-chlorophenyl)-2-(tetrazol-2-yl)ethyl ester of the following Formula 2:

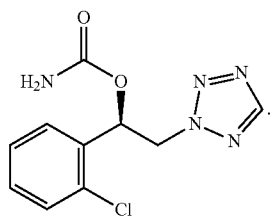

[Formula 2]

In one embodiment of the present invention, the first hydrophilic excipient of a sugar alcohol is selected from the group consisting of mannitol, sorbitol, xylitol, lactitol, maltitol and erythritol.

In one embodiment of the present invention, the disintegrant in step (a) and step (c) is selected from the group consisting of sodium starch glycolate, croscarmellose sodium, low substituted hydroxypropylcellulose and crospovidone.

Accordingly, in one embodiment, the present invention provides a method for preparation of an orally disintegrating tablet, comprising:

(a) a step of mixing the following ingredients (1) to (3);
(1) a carbamate compound of Formula 1, an isomer thereof, or a pharmaceutically acceptable salt, solvate or hydrate thereof as an active ingredient;
(2) a hydrophilic excipient consisting of a first hydrophilic excipient of a sugar alcohol selected from the group consisting of mannitol, sorbitol, xylitol, lactitol, maltitol and erythritol; and a second hydrophilic excipient selected from the group consisting of starch, microcrystalline cellulose, hydroxypropylcellulose and lactose; and
(3) a disintegrant selected from the group consisting of sodium starch glycolate, croscarmellose sodium, low substituted hydroxypropylcellulose and crospovidone;
(b) a step of preparing a granule by wet granulation using the mixture of step (a);
(c) a step of mixing the granule obtained from step (b) with a disintegrant selected from the group consisting of sodium starch glycolate, croscarmellose sodium, low substituted hydroxypropylcellulose and crospovidone; and
(d) a step of lubricating and tableting the mixture obtained from step (c).

In one embodiment of the present invention, the content of the carbamate compound is 2.5 to 25 wt % based on the total weight of the orally disintegrating tablet.

In one embodiment of the present invention, the content of the hydrophilic excipient is 65 to 90 wt % based on the total weight of the orally disintegrating tablet.

In one embodiment of the present invention, the weight ratio of the first hydrophilic excipient and the second hydrophilic excipient is 2:1 to 10:1, and preferably 4:1 to 8:1.

In one embodiment of the present invention, the content of the disintegrant in step (a) is 1 to 10 wt %, and preferably 2 to 5 wt % based on the total weight of the orally disintegrating tablet.

In one embodiment of the present invention, the disintegrant in step (c) contains 60 to 80% of particles having a particle size of 40 to 600 μm, and the content thereof is 4 to 8 wt % based on the total weight of the orally disintegrating tablet.

The present invention also provides an orally disintegrating tablet prepared by the above method.

In one embodiment of the present invention, the orally disintegrating tablet is used for the treatment of anxiety, depression, convulsion, epilepsy, migraine, bipolar disorder, drug abuse, smoking, attention deficit hyperactivity disorder (ADHD), obesity, sleep disorders, neuropathic pain, stroke, cognitive disorders, neurodegeneration or muscle spasm.

Effect of the Invention

The orally disintegrating tablet according to the present invention can be administered to patients suffering from discomfort and difficulty in swallowing the carbamate compound of Formula 1 or 2, thereby increase the patients' medication compliance. In particular, it is possible to administer the drug to patients with epilepsy who need to prevent further seizures by maintaining the blood concentration of the drug above the therapeutic concentration, so that the recurrence of further seizures can be prevented, and severe nerve damage and after-effects can be prevented. The orally disintegrating tablet prepared by the method according to the present invention exhibits excellent storage stability due to its high hardness and low friability, exhibits a rapid disintegration rate in the oral cavity and has excellent effect of having little foreign body sensation and residual feeling.

DETAILED DESCRIPTION

Figure 1:
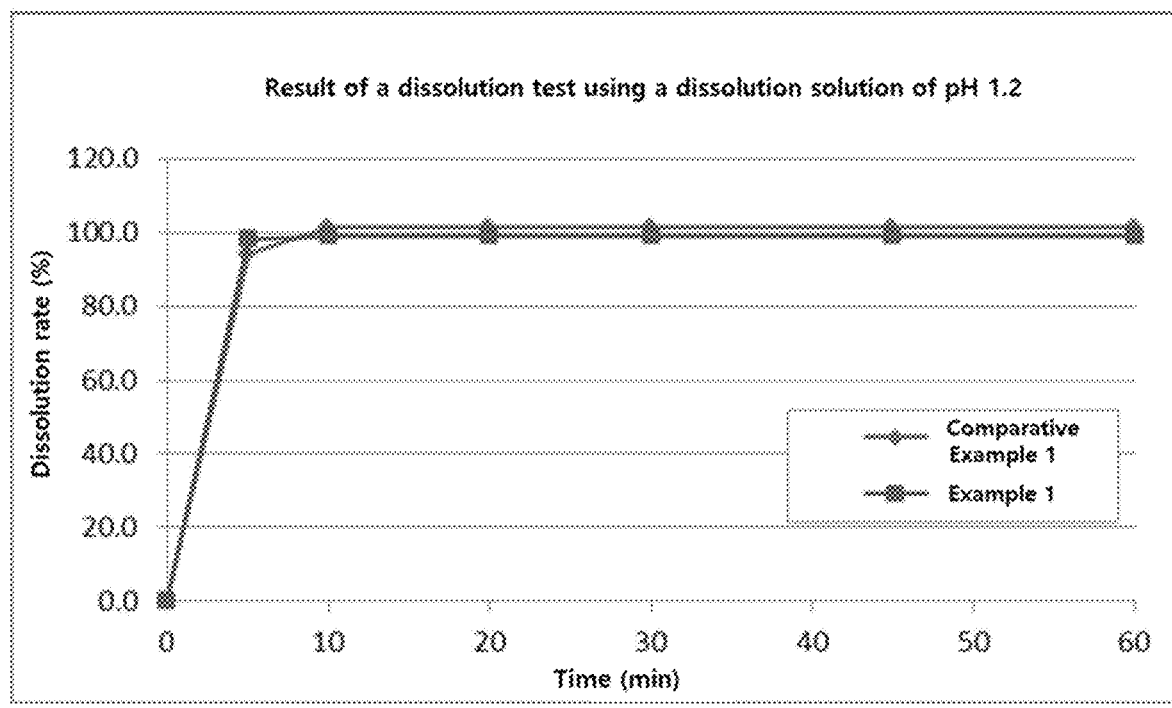
FIG. 1 is results of the dissolution test in Experimental Example 1 using the tablets prepared in Example 1 and Comparative Example 1.

Hereinafter, the present invention will be described in detail.

One embodiment of the present invention relates to an orally disintegrating tablet comprising:

(i) a granule prepared by wet granulation to comprise the following ingredients:
 (1) a carbamate compound of the following Formula 1, an isomer thereof, or a pharmaceutically acceptable salt, solvate or hydrate thereof as an active ingredient;
 (2) a hydrophilic excipient consisting of a first hydrophilic excipient of a sugar alcohol; and a second hydrophilic excipient selected from the group consisting of starch, microcrystalline cellulose, hydroxypropylcellulose and lactose; and
 (3) a disintegrant; and
(ii) a disintegrant which is mixed with the granule of (i):

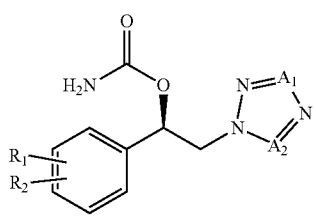

[Formula 1]

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

Another embodiment of the present invention relates to a method for preparation of an orally disintegrating tablet, comprising:

(a) a step of mixing the following ingredients (1) to (3);
 (1) a carbamate compound of Formula 1, an isomer thereof, or a pharmaceutically acceptable salt, solvate or hydrate thereof as an active ingredient;
 (2) a hydrophilic excipient consisting of a first hydrophilic excipient of a sugar alcohol; and a second hydrophilic excipient selected from the group consisting of starch, microcrystalline cellulose, hydroxypropylcellulose and lactose; and
 (3) a disintegrant;
(b) a step of preparing a granule by wet granulation using the mixture of step (a);
(c) a step of mixing the granule obtained from step (b) with a disintegrant; and
(d) a step of lubricating and tableting the mixture obtained from step (c).

In one embodiment of the present invention, in Formula 1, $R_1$ and $R_2$ are each independently selected from the group consisting of hydrogen, halogen and $C_1$-$C_8$ alkyl.

In one embodiment of the present invention, the halo-$C_1$-$C_8$ alkyl is perfluoroalkyl.

In one embodiment of the present invention, the carbamate compound of Formula 1 is carbamic acid (R)-1-(2-chlorophenyl)-2-(tetrazol-2-yl)ethyl ester of the following Formula 2:

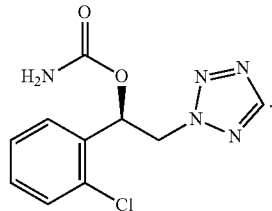

[Formula 2]

The term "compound" or "active ingredient" is a concept that encompasses not only the compound itself but also its isomers, or pharmaceutically acceptable salts, solvates and hydrates thereof altogether. Accordingly, as used herein, the carbamate compound of Formula 1 refers to not only the compound but also its isomers, or pharmaceutically acceptable salts, solvates or hydrates thereof. Likewise, as used herein, the carbamate compound of Formula 2 refers to not only the carbamic acid (R)-1-(2-chlorophenyl)-2-(tetrazol-2-yl)ethyl ester but also its isomers, or pharmaceutically acceptable salts, solvates or hydrates thereof.

Examples of the pharmaceutically acceptable salts of the carbamate compound of Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc, etc.

A person having ordinary skill in the art of synthesis of compounds could have easily prepared the carbamate compound of Formula 1 or 2 using known compounds or compounds which can be easily prepared therefrom. In particular, methods for preparing the compound of Formula 1 are described in detail in PCT Publication Nos. WO 2006/112685 A1, WO 2010/150946 A1 and WO 2011/046380 A2, the disclosures of which are incorporated herein by reference. The compound of Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

Specifically, the orally disintegrating tablet may comprise the carbamate compound of Formula 1 or 2 in an amount of 2.5 to 25 wt %, or 5 to 10 wt % per tablet. In another embodiment, the orally disintegrating tablet of the present invention may comprise said active ingredient in an amount of 1 to 30 mg, or 10 to 20 mg.

In one embodiment of the present invention, the orally disintegrating tablet comprises granules prepared by wet granulation method and a disintegrant mixed with the granules.

The method for preparing the orally disintegrating tablet comprises a step of preparing granules by wet granulation method and a step of mixing the granules obtained in the above step with a disintegrant. Specifically, a carbamate compound of Formula 1, a hydrophilic excipient and a disintegrant are mixed with water and the mixture is granulated. The wet-granules can then be dried.

The type and amount of the hydrophilic excipient added in the wet granulation step is very important. If the hydrophilic excipient has a high molecular weight or a high viscosity, the excipient forms a high-viscosity gel when it is hydrated by saliva in the oral cavity. In this case, it is difficult to achieve rapid disintegration in the oral cavity and there may be an unpleasant feeling in the oral cavity.

The hydrophilic excipient comprises a first hydrophilic excipient of a sugar alcohol; and a second hydrophilic excipient selected from the group consisting of starch, microcrystalline cellulose, hydroxypropylcellulose and lactose. The content of the hydrophilic excipient may be 65 to 90 wt %, and specifically 75 to 85 wt % based on the total weight of the orally disintegrating tablet.

In one embodiment of the present invention, the first hydrophilic excipient of a sugar alcohol may be one or more selected from the group consisting of mannitol, sorbitol, xylitol, lactitol, maltitol and erythritol. Specifically, it may be mannitol.

In one embodiment of the present invention, examples of the starch in the second hydrophilic excipient include corn starch, pregelatinized starch, potato starch, wheat starch, glutinous rice starch, sweet potato starch, tapioca starch, rice starch, waxy corn starch, and the like, but they are not limited thereto. In one embodiment of the present invention, the second hydrophilic excipient may be pregelatinized starch.

In one embodiment of the present invention, the hydrophilic excipient may be a mixture of a sugar alcohol and starch, and more specifically a mixture of mannitol and starch, but it is not limited thereto. The orally disintegrating tablet of the present invention may be prepared by combining two or more of other hydrophilic excipients having properties similar to that of each selected from the first hydrophilic excipient and the second hydrophilic excipient.

In one embodiment of the present invention, the weight ratio of the first hydrophilic excipient and the second hydrophilic excipient may be 2:1 to 10:1, specifically 4:1 to 8:1, and more specifically 5:1 to 7:1. By appropriately adjusting the ratio of the first hydrophilic excipient and the second hydrophilic excipient, it is possible to prepare an orally disintegrating tablet that is capable of rapidly disintegrating in the oral cavity and has an excellent hardness and friability.

In order to prepare an orally disintegrating tablet capable of rapidly disintegrating in the oral cavity, the appropriate composition and amount of the first disintegrant added in the step of wet granulation and the second disintegrant added in the step of mixing with granules are important. The first disintegrant added in the step of wet granulation may be the same as or different from the second disintegrant added in the step of mixing with granules.

The disintegrant as the first disintegrant added in the step of wet granulation or added in granules may be one or more selected from the group consisting of sodium starch glycolate, croscarmellose sodium, low substituted hydroxypropylcellulose and crospovidone. Specifically, it may be sodium starch glycolate. The content of the disintegrant is 1 to 10 wt %, and specifically 2 to 5 wt % based on the total weight of the orally disintegrating tablet.

In one embodiment, during the above wet granulation step, the hydrophilic excipient can be mixed after the active ingredient and the disintegrant are mixed.

In one embodiment, wet granule and the second disintegrant may be dry-blended.

The disintegrant as the second disintegrant added in the step of mixing with granules may be one or more selected from the group consisting of sodium starch glycolate, croscarmellose sodium, low substituted hydroxypropylcellulose and crospovidone. Specifically, it may be crospovidone. The content of the disintegrant is preferably 4 to 8 wt % based on the total weight of the orally disintegrating tablet. The disintegrant, which is added during the step of mixing with granules, may contain 60 to 80% of particles having a particle size of 40 to 600 µm. Among them, at least 80% of particles may have a size of 40 to 100 µm. If the disintegrant satisfying said conditions is selected, it is possible to prepare an orally disintegrating tablet having minimized foreign body sensation and residual feeling, high hardness and low friability.

In one embodiment of the present invention, the orally disintegrating tablet may contain about 2.5 to 25 wt %, about 3 to 20 wt %, or about 5 to 10 wt % of the carbamate compound of Formula 1; about 65 to 90 wt %, or about 75 to 85 wt % of the hydrophilic excipient; and about 5 to 18 wt %, or about 6 to 13 wt % of the disintegrant based on the total weight of the tablet.

The orally disintegrating tablet may comprise a lubricant, a glidant and a sweetening agent, etc.

In one embodiment of the present invention, magnesium stearate, calcium stearate, zinc stearate, talc, wax, boric acid, hydrogenated vegetable oil, sodium chlorate, magnesium lauryl sulfate, sodium oleate, sodium acetate, sodium benzoate, polyethylene glycol, stearic acid, fatty acid, sodium stearyl fumarate, sodium lauryl sulfate and mixtures thereof may be used as an appropriate lubricant, but it is not limited thereto. Preferably, the lubricant is magnesium stearate or sodium lauryl sulfate. The content of the lubricant may be 0.1 to 5 wt % based on the total weight of the orally disintegrating tablet.

In one embodiment of the present invention, silica; colloidal silicon dioxide and talc, etc. may be used as an appropriate glidant, but it is not limited thereto.

In one embodiment of the present invention, aspartame, potassium acesulfame, sodium saccharinate, neohesperidin dihydrochalcone, sucralose, saccharin, sugars (for example, sucrose, glucose, lactose and fructose), a sugar alcohol (for example, mannitol, sorbitol, xylitol and erythritol) and mixtures thereof may be used as an appropriate sweetener, but it is not limited thereto. Preferably, the sweetener is aspartame, sucralose and/or saccharin. The content of the sweetener may be 0.1 to 5 wt %, and preferably 0.2 to 3 wt % based on the total weight of the orally disintegrating tablet.

A flavoring agent and a pigment preservative agent, etc. may be further added as other additives.

The orally disintegrating tablet may be disintegrated in the oral cavity within 60 seconds or 30 seconds, and specifically within 20 seconds when measured according to the disintegration test of Korean Pharmacopeia (11th edition).

In addition, from the orally disintegrating tablet, at least 80% of the active ingredient may be eluted within 10 minutes, or at least 90% of the active ingredient may be eluted within 15 minutes when eluted by the No. 2 method (Paddle method, apparatus 2) with the dissolution test No. 1 solution (900 ml), at 50 revolutions/min at 37° C. according to Korean Pharmacopeia (11th edition).

In addition, the hardness and the friability of the orally disintegrating tablet may be measured in a conventional manner. As a result of measurement in such a manner, the hardness is 6 to 12 kp and the friability is 1.0% or less, which means a high storage stability. Specifically, since the hardness is 9 to 11 kp and the friability is 0.6% or less, the storage stability is high.

The orally disintegrating tablet may be used for the treatment of anxiety, depression, convulsion, epilepsy, migraine, bipolar disorder, drug abuse, smoking, attention deficit hyperactivity disorder (ADHD), obesity, sleep disorders, neuropathic pain, stroke, cognitive disorders, neurodegeneration or muscle spasm.

The dosage of the carbamate compound of Formula 1 or 2 for the prevention, alleviation or treatment of the above diseases may typically vary depending on the severity of the disease, the body weight and the metabolic status of the subject. A "therapeutically effective amount" for an individual patient refers to an amount sufficient to achieve a therapeutic effect. Specifically, the therapeutically effective amount of the compounds of the present invention is 50 to 500 mg, 50 to 400 mg, 50 to 300 mg, 100 to 400 mg, 100 to 300 mg, 50 to 200 mg, or 100 to 200 mg, based on the free form and once-daily administration to humans. The therapeutically effective amount is preferably 50 to 300 mg, more preferably 50 to 200 mg.

The usage and dosage of the orally disintegrating tablet of the present invention are determined depending on the patient's gender, age and other conditions, the disease state and the like. In one embodiment, the orally disintegrating tablet of the present invention may be administered twice to four times a day at 4 to 12 hour intervals, and the dosage and interval may be adjusted as necessary.

The orally disintegrating tablet prepared by the method according to the present invention exhibits excellent storage stability due to its high hardness and low friability, exhibits a rapid disintegration rate in the oral cavity at the same time, and has excellent effect of having little foreign body sensation and residual feeling. This is made possible by the appropriate combination and amount of the two types of hydrophilic excipients and by the appropriate combination of the disintegrant. In addition, the wet granulation method, which is a relatively simple and economical method, is used to minimize foreign body sensation and residual feeling.

Hereinafter, the present invention will be explained in more detail through working examples. However, the following working examples are only intended to illustrate one or more embodiments and are not intended to limit the scope of the invention.

EXAMPLES

Preparation Example

Synthesis of carbamic acid (R)-1-(2-chlorophenyl)-2-(tetrazol-2-yl)ethyl ester

Carbamic acid (R)-1-(2-chlorophenyl)-2-(tetrazol-2-yl)ethyl ester (the compound of Formula 2, hereinafter referred to as "the test compound") was prepared according to the method described in Preparation Example 50 of PCT Publication No. WO 2010/150946.

Examples 1 and 2

Preparation of Orally Disintegrating Tablets

Carbamic acid (R)-1-(2-chlorophenyl)-2-(tetrazol-2-yl)ethyl ester and sodium starch glycolate were mixed in a composition as shown in Table 1 below and sieved through a 30 mesh sieve. Mannitol and pregelatinized starch were mixed and the mixture was sieved through a 30 mesh sieve, which was used previously, to wash the sieve. An appropriate amount of purified water was added to the mixture. The granule mixture was dried in an oven at 60° C. for 1 hour, crospovidone was added thereto, and then they were dry-blended. After the dry post-mix was completed, magnesium stearate was sieved thereto with a 40 mesh sieve to lubricate. And then, the mixture was tableted with a single-punch tablet press (ERWEKA) to prepare an orally disintegrating tablet of 200 mg dose per tablet.

TABLE 1

Compositions of the tablets of Examples 1 and 2

| Ingredients | Example 1 wt % | Example 2 wt % |
|---|---|---|
| Carbamic acid (R)-1-(2-chlorophenyl)-2-(tetrazol-2-yl)ethyl ester | 5.0 | 10.0 |
| Mannitol | 69.75 | 67.25 |
| Pregelatinized starch | 12.5 | 10 |
| Sodium starch glycolate | 4.5 | 4.5 |
| Purified water | 1.2 mL per tablet | 1.0 mL per tablet |
| Crospovidone | 6.35 | 6.35 |
| Magnesium stearate | 0.9 | 0.9 |
| Flavoring agent | 1.0 | 1.0 |
| Total | 100 | 100 |

Comparative Examples 1 and 2

Preparation of Immediate-Release Tablets

Carbamic acid (R)-1-(2-chlorophenyl)-2-(tetrazol-2-yl)ethyl ester and colloidal silicon dioxide were mixed in the composition as shown in Table 2 below and sieved through a 30 mesh sieve. Microcrystalline cellulose, lactose monohydrate and sodium starch glycolate were mixed and the mixture was sieved through a 30 mesh sieve, which was used previously, to wash the sieve, and then mixed. Magnesium stearate was sieved through a 40 mesh sieve and added to the mixture to lubricate. And then, the mixture was tableted with a single-punch tablet press (ERWEKA) to prepare an immediate-release tablet of 200 mg dose per tablet.

TABLE 2

Compositions of the tablets of Comparative Examples 1 and 2

| Ingredients | Comparative Example 1 wt % | Comparative Example 2 wt % |
|---|---|---|
| Carbamic acid (R)-1-(2-chlorophenyl)-2-(tetrazol-2-yl)ethyl ester | 5.0 | 10.0 |
| Microcrystalline cellulose | 53.07 | 48.07 |
| Lactose monohydrate | 35.25 | 35.25 |
| Sodium starch glycolate | 4.5 | 4.5 |
| Colloidal silicon dioxide | 1.0 | 1.0 |
| Magnesium stearate | 1.18 | 1.18 |
| Total | 100 | 100 |

Experimental Example 1

Dissolution and Disintegration Test and Evaluation a. Dissolution Test

Each of the orally disintegrating tablets prepared in Example 1 and the immediate-release tablets prepared in Comparative Example 1 was tested and evaluated by the apparatus and the tester described in dissolution test in the Korean Pharmacopeia (11th edition). The test was carried out under No. 2 test (Paddle method, apparatus 2) with the dissolution test No. 1 solution (900 ml), at 50 revolutions/min at 37° C. As a result, Example 1 and Comparative Example 1 showed the same dissolution results. The resulting graph is shown in FIG. 1.

b. Disintegration Test

The orally disintegrating tablets and the immediate-release tablets prepared in Examples 1 and 2, and Comparative Examples 1 and 2, respectively, were tested in No. 1 solution with the apparatus and the tester described in the disintegration test in the Korean Pharmacopeia (11th edition), and six (6) test results were averaged. The results are shown in Table 3 below.

TABLE 3

Results of the disintegration test

| | Disintegration rate (sec) |
|---|---|
| Comparative Example 1 | 31 |
| Comparative Example 2 | 35 |
| Example 1 | 15 |
| Example 2 | 14 |

As shown in Table 3, the orally disintegrating tablets of Examples 1 and 2 showed a much faster disintegration rate than the immediate-release tablets of Comparative Examples 1 and 2.

Experimental Example 2

Evaluation of Ease of Movement and Storage of the Tablets

Measurement of Hardness and Friability

The hardness of the tablet was determined by using HDT-300 of LOGAN INSTRUMENT CORP. for each of six (6) tablets, and the average value was recorded. The friability of the tablet was determined by using FRIABILATOR of KUKJE ENG. CO. and the results were recorded by averaging the results of three trials conducted on a set of ten tablets. The results of the test are shown in Table 4 below.

TABLE 4

Results of measurement of hardness and friability

| | Hardness (kp) | Friability (%) |
|---|---|---|
| Comparative Example 1 | 14.1 | 0.41 |
| Comparative Example 2 | 13.3 | 0.28 |
| Example 1 | 10.4 | 0.54 |
| Example 2 | 10.6 | 0.32 |

As shown in Table 4, the orally disintegrating tablets of Examples 1 and 2 showed hardness and friability comparable to those of the immediate-release tablets of Comparative Examples 1 and 2, despite their property of immediate disintegration in the oral cavity.

Experimental Example 3

Figure 2:
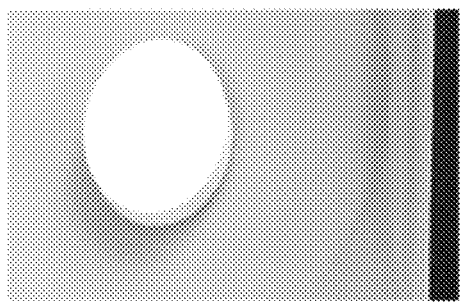
FIG. 2 is results of the hygroscopicity measurement test in Experimental Example 3 using the tablets prepared in Example 2 and Comparative Example 2.
Figure 2:
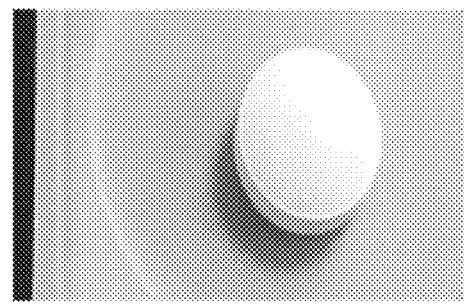
Figure 2:
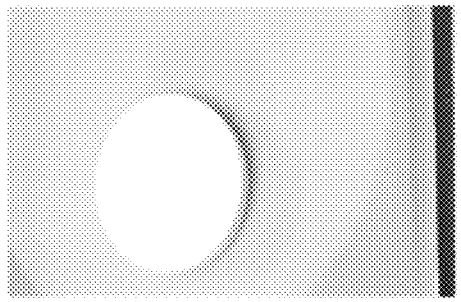
Figure 2:
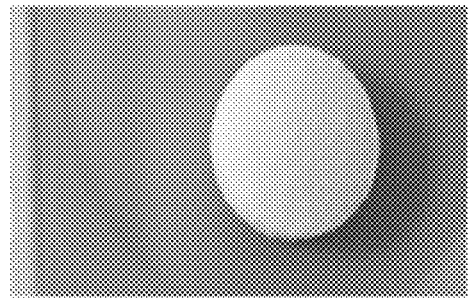
Figure 2:
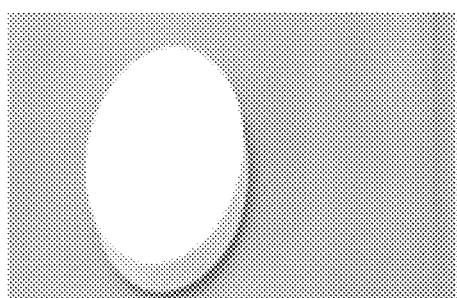
Figure 2:
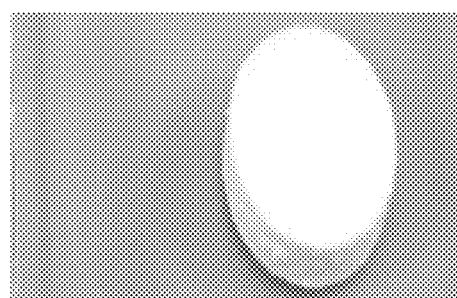

Evaluation of Possibility of Disintegration in the oral-mimic condition a. Hygroscopicity Measurement To simulate the oral environment, the interior of the desiccator was saturated with a supersaturated solution of potassium hydrogen phosphate to form a condition of relative humidity of 95%. The tablets of Example 2 and Comparative Example 2 were put in said desiccator of relative humidity of 95% without packing, and change was observed. As a result, the tablet of Comparative Example 2 showed no change caused by external humidity. In contrast, the surface of the tablet of Example 2 was roughened and swollen by humidification. Therefore, it was anticipated that the tablet of Example 2 would be rapidly disintegrated in the high-humidity oral condition in which saliva is present (see FIG. 2).

b. Tests for Measurement of Wetting Time and Determination of Change of Tablet Due to Pressure The tissues were spread on a chalet and wetted with artificial saliva. Then the tablets of Example 2 and Comparative Example 2 were each placed thereon, and the time during which the tablet was completely wetted was measured. In addition, the same pressure was applied to each tablet which was completely wet, and their state was observed.

Figure 3:
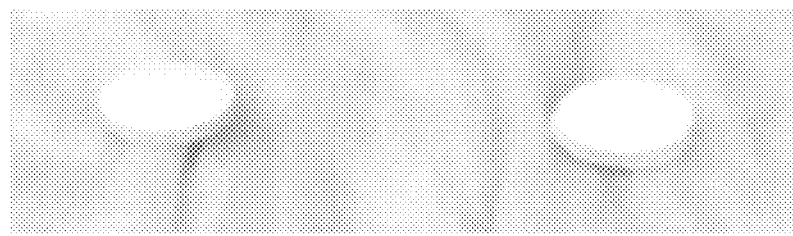
FIG. 3 is results of the wetting time test in Experimental Example 3 using the tablets prepared in Example 2 and Comparative Example 2.
Figure 3:
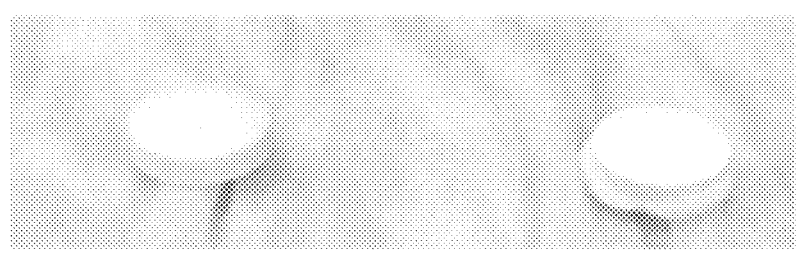
Figure 3:
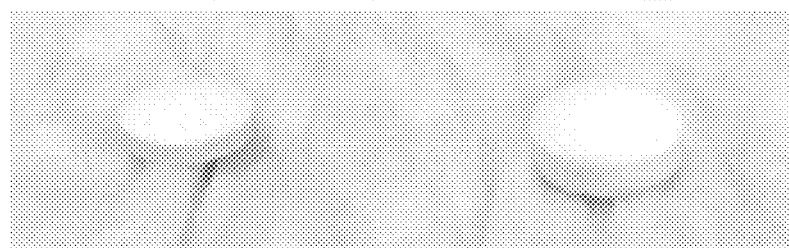
Figure 4:
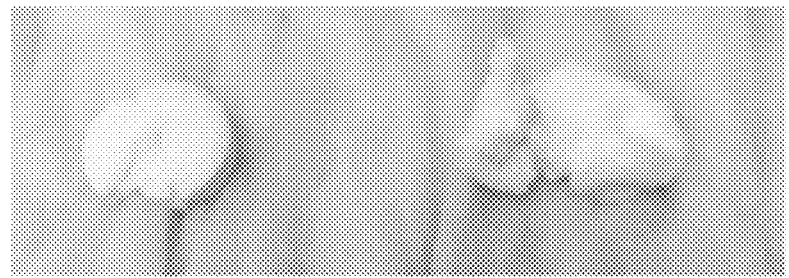
FIG. 4 is results of the test for change of tablet due to pressure in the oral cavity in Experimental Example 3 using the tablets prepared in Example 2 and Comparative Example 2.

As a result of the test, in the tablet of Example 2, the entire tablet was wet and swollen in 45 seconds. In contrast, the tablet of Comparative Example 2 did not wet as a whole even after 60 seconds (see FIG. 3). In addition, as a result of applying the same pressure using a spoon, the tablet of Comparative Example 2 was pressed while maintaining the tablet shape (see the photo on the left of FIG. 4), but the shape of the tablet of Example 2 was completely destroyed (see the photo on the right of FIG. 4).

Therefore, it was anticipated that when the tablet is exposed to high-humidity conditions in the oral cavity after ingestion and is then subjected to pressure by the roof of the mouth, the tablets of Example 2 would show excellent disintegrability.

Experimental Example 4

Evaluation of Possibility of Foreign Body Sensation and Residual Feeling

Figure 5:
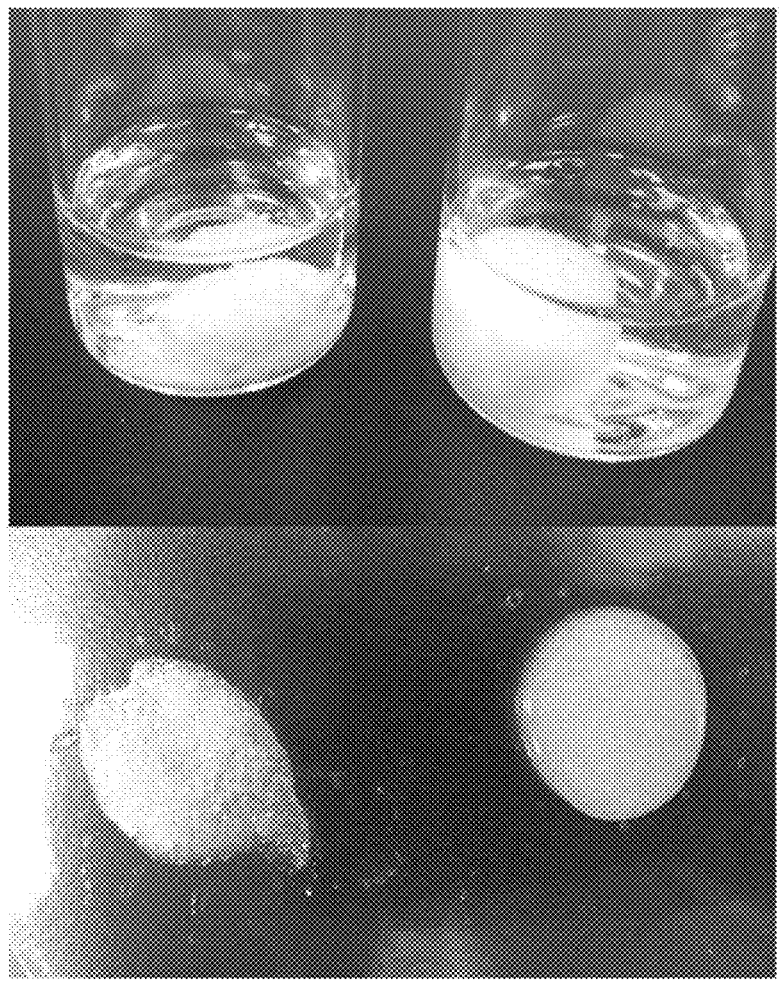
FIG. 5 is photos of disintegration of the tablets in artificial saliva in Experimental Example 4 using the tablets prepared in Example 1 and Comparative Example 1, and the resulting disintegrated solutions.
Figure 6:
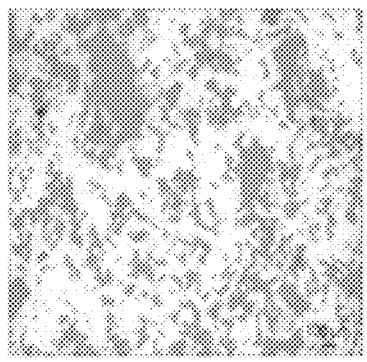
FIG. 6 is electron micrographs of the resulting disintegrated solutions of the tablets in artificial saliva in Experimental Example 4 using the tablets prepared in Example 2 and Comparative Example 2.
Figure 6:
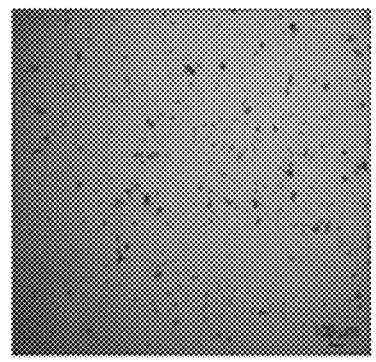
Figure 6:
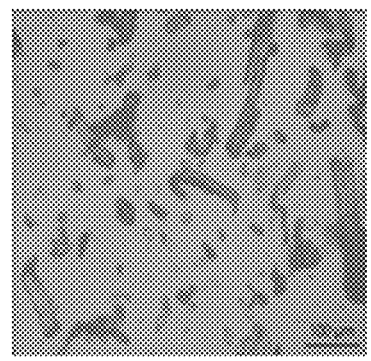
Figure 6:
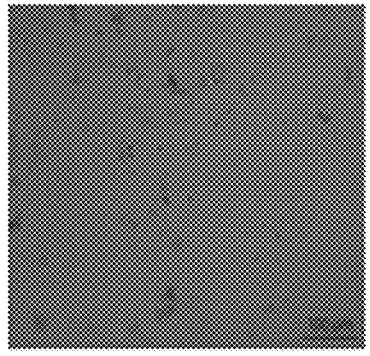

Microscopic Measurement of Solution Resulting from Disintegration in Artificial Saliva The tablets of Example 2 and Comparative Example 2 were each put into artificial saliva, and their disintegration was observed. After disintegration, the solution was taken and magnified 50 times and 200 times with a microscope (OLYMPUS) for evaluating the possibility of foreign body sensation and residual feeling. As a result, in the case of the tablet of Comparative Example 2, a particle size of 100 μm or more was observed. In case of the tablet of Example 2, however, a particle size of several μm was observed, which indicates that there will be almost no foreign body sensation and residual feeling (see FIGS. 5 and 6).

What is claimed is:

1. An orally disintegrating tablet comprising:
    (i) a granule prepared by wet granulation to comprise the following ingredients:
        (1) a carbamate compound of the following Formula 1, an isomer thereof, or a pharmaceutically acceptable salt, solvate or hydrate thereof as an active ingredient;
        (2) a hydrophilic excipient consisting of a first hydrophilic excipient of a sugar alcohol; and a second hydrophilic excipient selected from the group consisting of starch, microcrystalline cellulose, hydroxypropylcellulose and lactose; and
        (3) a disintegrant; and
    (ii) a disintegrant which is mixed with the granule of (i):

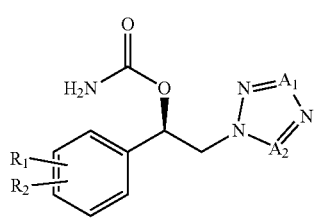

[Formula 1]

wherein,
$R_1$ and $R_2$ are each independently selected from the group consisting of hydrogen, halogen, $C_1$-$C_8$ alkyl and
one of $A_1$ and $A_2$ is CH, and the other is N,
wherein the weight ratio of the first hydrophilic excipient and the second hydrophilic excipient is 2:1 to 10:1.

2. The orally disintegrating tablet according to claim 1, wherein the carbamate compound of Formula 1 is carbamic acid (R)-1-(2-chlorophenyl)-2-(tetrazol-2-yl)ethyl ester of the following Formula 2:

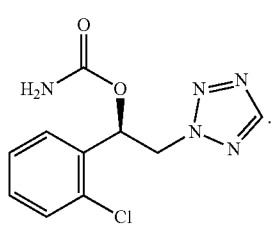

[Formula 2]

3. The orally disintegrating tablet according to claim 1, wherein the first hydrophilic excipient of a sugar alcohol is selected from the group consisting of mannitol, sorbitol, xylitol, lactitol, maltitol and erythritol.

4. The orally disintegrating tablet according to claim 1, wherein the disintegrant in the above (i) and (ii) is selected from the group consisting of sodium starch glycolate, croscarmellose sodium, low substituted hydroxypropylcellulose and crospovidone.

5. The orally disintegrating tablet according to claim 1, wherein the content of the carbamate compound is 2.5 wt % to 25 wt % based on the total weight of the orally disintegrating tablet.

6. The orally disintegrating tablet according to claim 1, wherein the content of the hydrophilic excipient is 65 wt % to 90 wt % based on the total weight of the orally disintegrating tablet.

7. The orally disintegrating tablet according to claim 1, wherein the content of the disintegrant in the granule of (i) is 1 wt % to 10 wt % based on the total weight of the orally disintegrating tablet.

8. The orally disintegrating tablet according to claim 1, the disintegrant mixed in (ii) contains 60% to 80% of particles having a particle size of 40 μm to 600 μm, and the content thereof is 4 wt % to 8 wt % based on the total weight of the orally disintegrating tablet.

9. The orally disintegrating tablet according to claim 1 for use in the treatment of anxiety, depression, convulsion, epilepsy, migraine, bipolar disorder, drug abuse, smoking, attention deficit hyperactivity disorder (ADHD), obesity, sleep disorders, neuropathic pain, stroke, cognitive disorders, neurodegeneration or muscle spasm.

10. A method for preparation of an orally disintegrating tablet, comprising:
    (a) a step of mixing the following ingredients (1) to (3);
        (1) a carbamate compound of the following Formula 1, an isomer thereof, or a pharmaceutically acceptable salt, solvate or hydrate thereof as an active ingredient;
        (2) a hydrophilic excipient consisting of a first hydrophilic excipient of a sugar alcohol; and a second hydrophilic excipient selected from the group consisting of starch, microcrystalline cellulose, hydroxypropylcellulose and lactose; and
        (3) a disintegrant;
    (b) a step of preparing a granule by wet granulation using the mixture of step (a);
    (c) a step of mixing the granule obtained from step (b) with a disintegrant; and
    (d) a step of lubricating and tableting the mixture obtained from step (c):

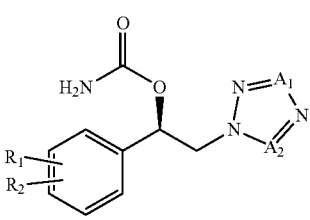

[Formula 1]

wherein,
$R_1$ and $R_2$ are each independently selected from the group consisting of hydrogen, halogen, $C_1$-$C_8$ alkyl, and
one of $A_1$ and $A_2$ is CH, and the other is N, wherein the weight ratio of the first hydrophilic excipient and the secon hydrophilic excipient is 2:1 to 10:1.

11. The method for preparation according to claim 10, wherein the carbamate compound of Formula 1 is carbamic acid (R)-1-(2-chlorophenyl)-2-(tetrazol-2-yl)ethyl ester of the following Formula 2:

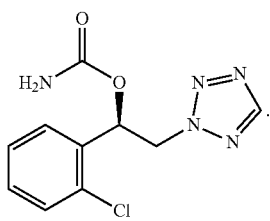

[Formula 2]

12. The method for preparation according to claim 10, wherein the first hydrophilic excipient of a sugar alcohol is selected from the group consisting of mannitol, sorbitol, xylitol, lactitol, maltitol and erythritol.

13. The method for preparation according to claim 10, wherein the disintegrant in step (a) and step (c) is selected from the group consisting of sodium starch glycolate, croscarmellose sodium, low substituted hydroxypropylcellulose and crospovidone.

14. The method for preparation according to claim 10, wherein the content of the carbamate compound is 2.5 wt % to 25 wt % based on the total weight of the orally disintegrating tablet.

15. The method for preparation according to claim 10, wherein the content of the hydrophilic excipient is 65 wt % to 90 wt % based on the total weight of the orally disintegrating tablet.

16. The method for preparation according to claim 10, wherein the content of the disintegrant in step (a) is 1 wt % to 10 wt % based on the total weight of the orally disintegrating tablet.

17. The method for preparation according to claim 10, wherein the disintegrant in step (c) contains 60% to 80% of particles having a particle size of 40 μm to 600 μm, and the content thereof is 4 wt % to 8 wt % based on the total weight of the orally disintegrating tablet.

18. An orally disintegrating tablet prepared by a method comprising (a) a step of mixing the following ingredients (1) to (3);
 (1) a carbamate compound of the following Formula 1, an isomer thereof, or a pharmaceutically acceptable salt, solvate or hydrate thereof as an active ingredient;
 (2) a hydrophilic excipient consisting of a first hydrophilic excipient of a sugar alcohol; and a second hydrophilic excipient selected from the group consisting of starch, microcrystalline cellulose, hydroxypropylcellulose and lactose; and
 (3) a disintegrant;
(b) a step of preparing a granule by wet granulation using the mixture of step (a):
(c) a step of mixing the granule obtained from step (b) with a disintegrant; and
(d) a step of lubricating and tableting the mixture obtained from step (c):

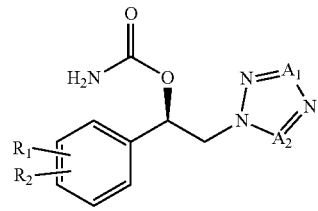

[Formula 1]

wherein,
R₁ and R₂ are each independently selected from the group consisting of hydrogen, halogen, and $C_1$-$C_8$ alkyl; and
one of A₁ and A₂ is CH, and the other is N,
wherein the weight ratio of the first hydrophilic excipient and the second hydrophilic excipient is 2:1 to 10:1.

19. The orally disintegrating tablet according to claim 18 for use in the treatment of anxiety, depression, convulsion, epilepsy, migraine, bipolar disorder, drug abuse, smoking, attention deficit hyperactivity disorder (ADHD), obesity, sleep disorders, neuropathic pain, stroke, cognitive disorders, neurodegeneration or muscle spasm.

* * * * *